US00PP21223P3

(12) United States Plant Patent
Budagovsky

(10) Patent No.: US PP21,223 P3
(45) Date of Patent: Aug. 24, 2010

(54) APPLE TREE ROOTSTOCK NAMED 'MICH 96'

(50) Latin Name: *Malus domestica*
Varietal Denomination: Mich 96

(76) Inventor: Valentin Ivanovich Budagovsky, Michurinsk (RU); Anatoly Ivanovich Zavrazhnov, legal representative, Internatsionalnaya 101, Tambov region, Michurinsk (RU) 393760

( * ) Notice: Subject to any disclaimer, the term of this patent is extended or adjusted under 35 U.S.C. 154(b) by 0 days.

(21) Appl. No.: 12/313,976

(22) Filed: Nov. 26, 2008

(65) Prior Publication Data

US 2010/0132081 P1 May 27, 2010

(51) Int. Cl.
*A01H 5/00* (2006.01)

(52) U.S. Cl. ..... Plt./174

(58) Field of Classification Search ..... Plt./174
See application file for complete search history.

*Primary Examiner*—Susan B McCormick Ewoldt
(74) *Attorney, Agent, or Firm*—The Webb Law Firm

(57) ABSTRACT

A new and distinct *Malus domestica* plant used as a rootstock that exhibits a vigorous root system and drought resistance.

5 Drawing Sheets

Botanical classification: *Malus domestica.*
Varietal denomination: 'Mich 96'.

BACKGROUND OF THE INVENTION

The present invention comprises a new and distinct cultivar of clonal *Malus domestica* used as a rootstock known by the varietal name 'Mich 96'. The new variety was discovered in the Tambov region of Russia in the early 1960s. The new variety is the result of a cross between semi-dwarf apple rootstock '13-14' (female parent, unpatented) and dwarf apple rootstock 'Paradiska Budagovskogo' also referred to as 'B9' or simply 'Bud 9') (male parent, unpatented). The purpose of the breeding program was to develop winter hardy rootstocks with good rooting, pest and disease resistance, and high productivity. The new variety exhibits similar anthocyanic colored leaves, bark, and wood to both parents, but has better rooting than both parents. Further, the new variety has anthocyanic shoots that are similar to 'Paradiska Budagovskogo' (B9), but has better hardiness, improved frost resistance, and higher output of layers per 1 hectare. The new variety has been trial and field tested and has been found to retain its distinctive characteristics and remain true to type through successive propagations. The following characteristics distinguish 'Mich 96' from other varieties known to a representative of the breeder:

1. 'Mich 96' has a vigorous root system;
2. The wood of 'Mich 96' is moderately strong and the variety does not require additional support;
3. 'Mich 96' endures temperatures as low as −15° C. to −16° C.;
4. The output of two year old 'Mich 96' trees grown in a nursery is 80-100%;
5. 'Mich 96' trees begin to bear fruit early at their $3^{rd}$ to $4^{th}$ year after planting and quickly increase in harvest volume;
6. The average yield capacity of 'Mich 96' is 20-25 trees per hectare;
7. 'Mich 96' is only minimally affected by pests and diseases;
8. 'Mich 96' is drought resistant; and 9. In the orchard, 'Mich 96' shows little to no young growth.

DESCRIPTION OF THE DRAWINGS

The accompanying photographic drawings illustrate the one year old 'Mich 96' rootstocks produced from layer propagation and grown in Dundee, Oreg. The color is as nearly true as is possible with color illustrations of this type.

DESCRIPTION OF THE PLANT

Figure 1:
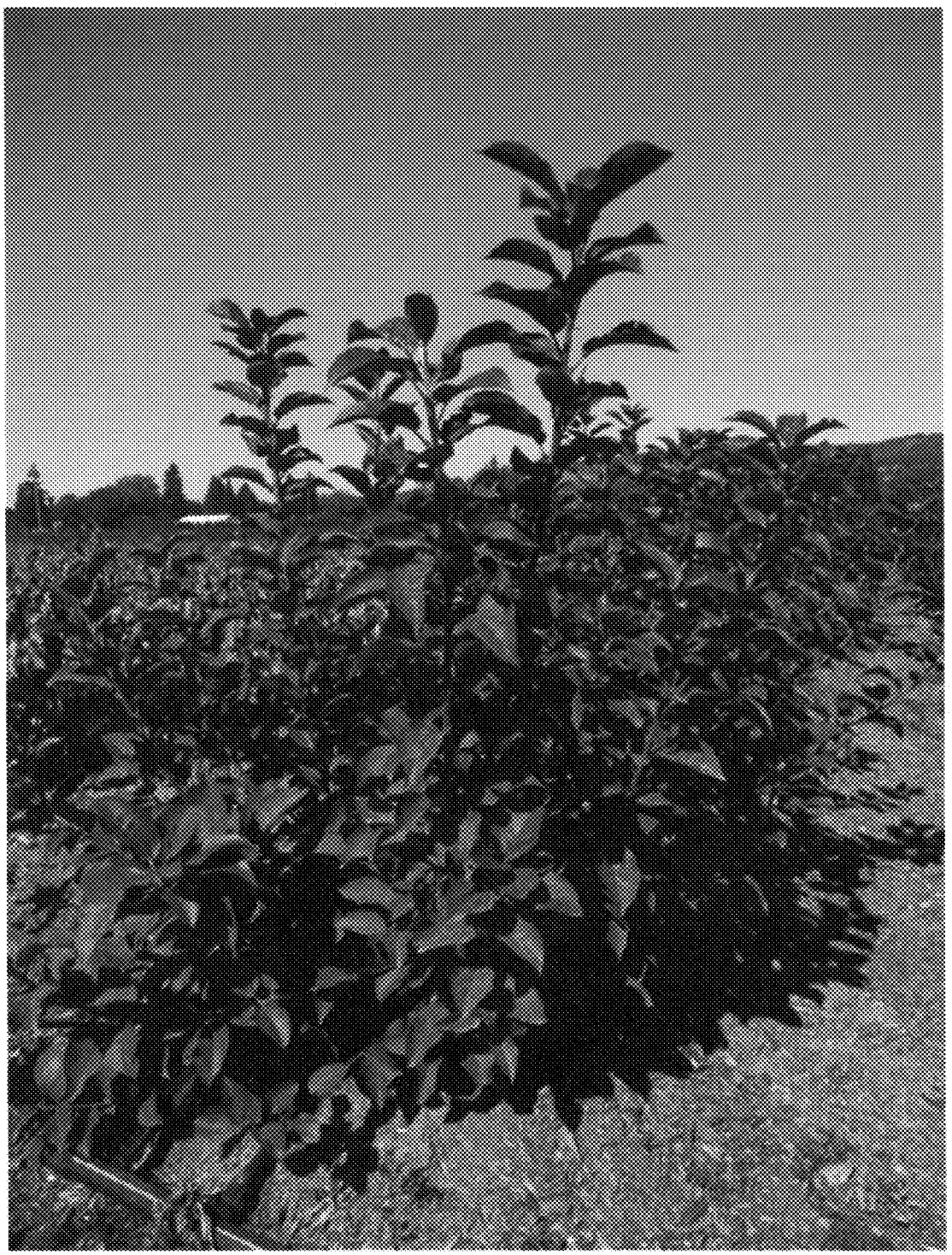
FIG. 1 shows 'Mich 96' rootstocks in layer beds.
Figure 2:
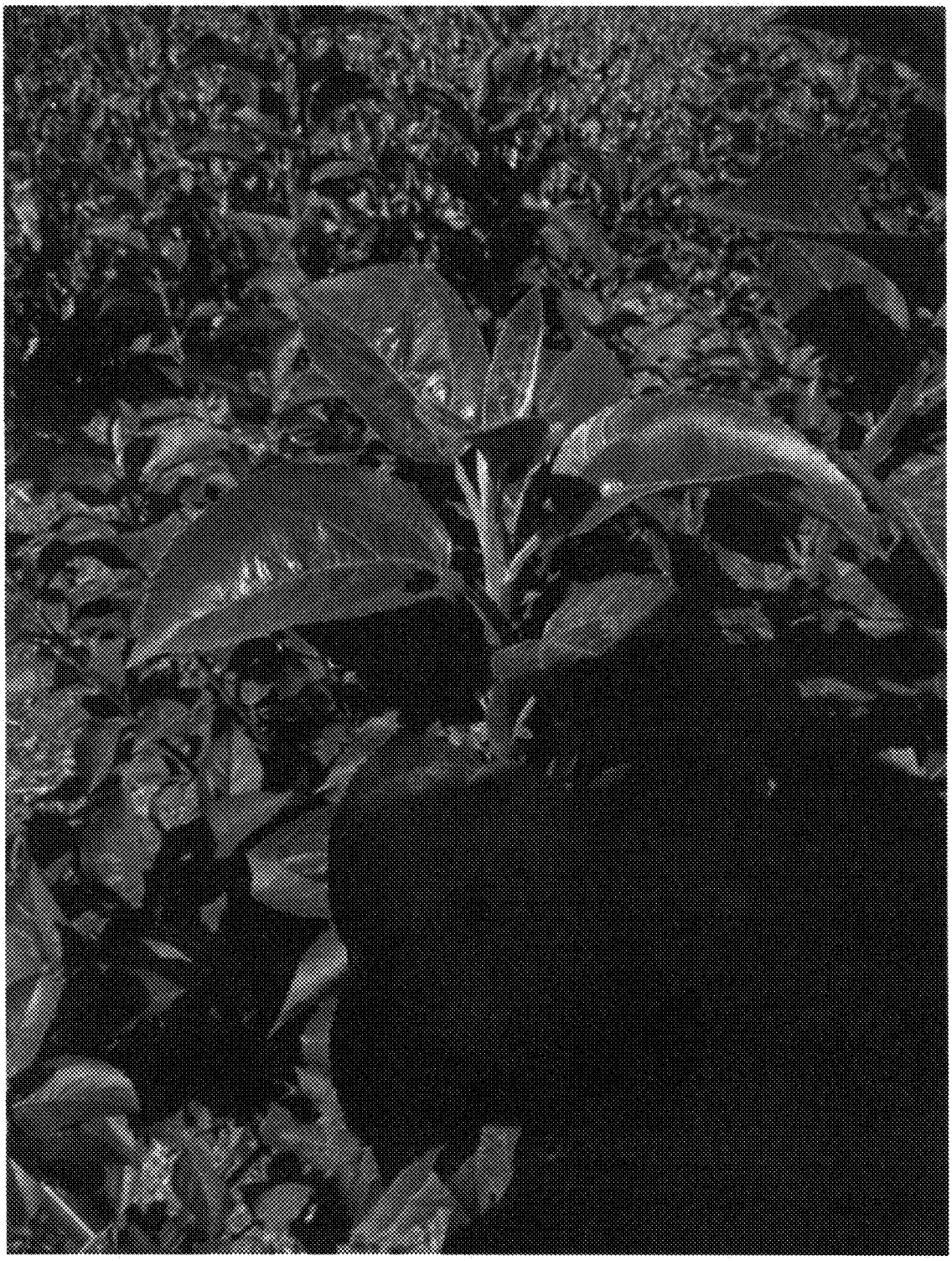
FIG. 2 is a close-up view of a 'Mich 96' rootstock.
Figure 3:
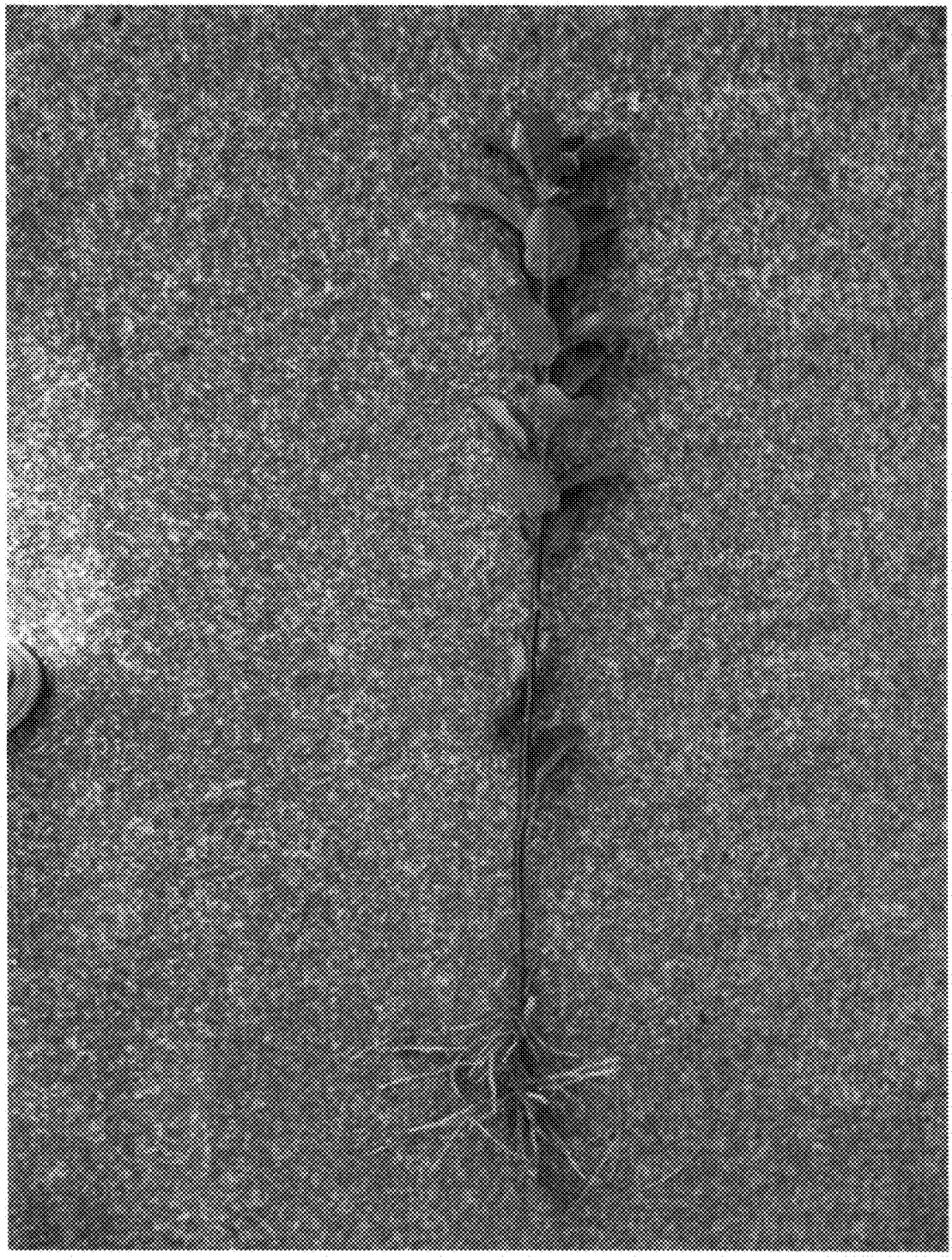
FIG. 3 is a view of an unrooted 'Mich 96' rootstock.
Figure 4:
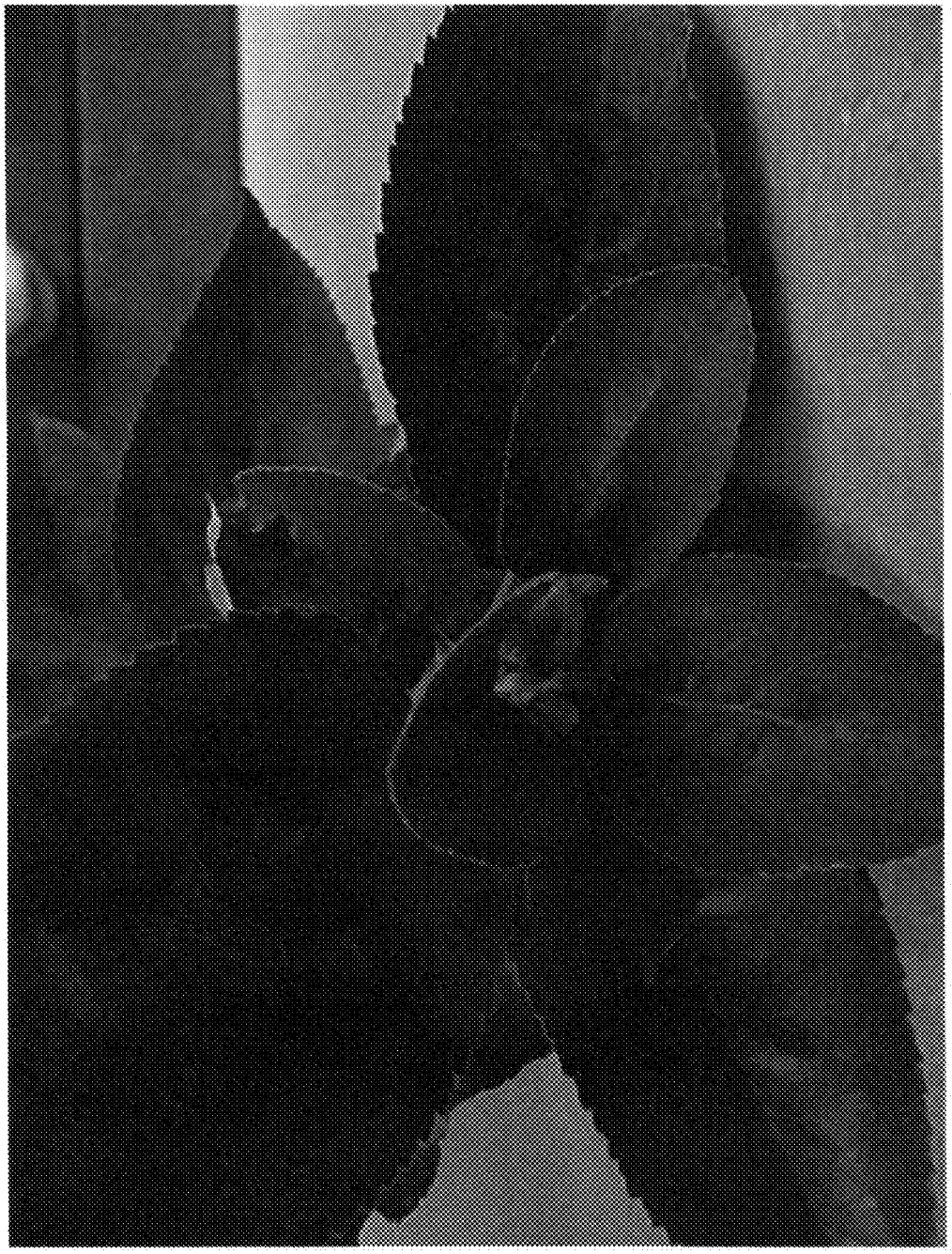
FIG. 4 is a close-up view of the leaves of the new variety.
Figure 5:
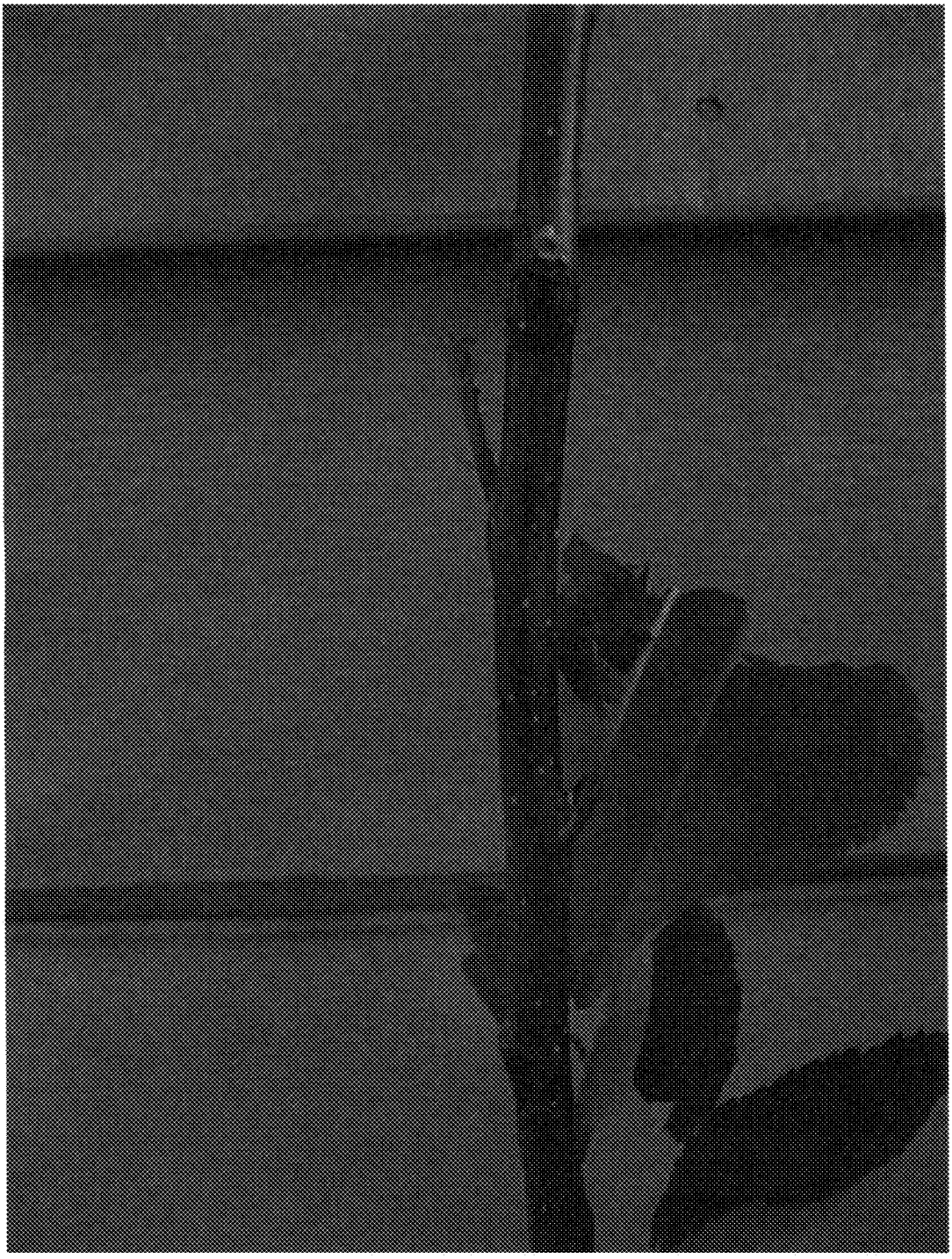
FIG. 5 is a close up view of the bark of the new variety.

The following detailed description sets forth the characteristics of the new cultivar. Some of the data which defines these characteristics was collected outside under natural daylight on plants produced by asexual reproductions via vertical layering propagation carried out in the Tambov region of Russia of Russia. However, some of the data was collected outside under natural daylight on one year old plants produced by asexual reproductions via vertical layering propagation carried out in Dundee, Oreg.; this data is indicated by an asterisk. When available, color references follow The R.H.S. Colour Chart of The Royal Horticultural Society of London.

TREE

Age: 10 years.
Size: 1.5 m.
Rooting*: Very strong; double the root mass when compared to apple rootstock 'Malling 9' rootstock.
Density: 5×2 m.
Form: Branching.
Production: Average.
Growth type: Apical.

Trunk:

*Size.*—10 cm in diameter.

*Surface texture.*—Rough.

*Bark color*.*—59A.

*Lenticels.*—Length: 1.7 mm. Width: 0.2 mm. Color: 155B. Shape*: Oval. Length*: 1.0 mm. Width*: 0.5 mm. Color*: 155D. Density*: Approximately 25 lenticels per centimeter.

Branches:

*Diameter.*—2.0 to 3.0 cm.

*Surface texture.*—Rough.

*Color.*—185A.

*Average crotch angle.*—Close to 90 degrees.

*Bud arrangement.*—Alternate and approximately 3.0 cm apart.

*Internode length*.*—Varies from 2.0 to 3.0 cm. Lenticels: Shape and size: Rounded and small. Color: Whitish.

Leaves:

*Length.*—About 85-115 mm.

*Width.*—About 60-80 mm.

*Form.*—Egg-shaped.

*Texture.*—Smooth.

*Apex.*—Acute, with light pubescence relative to the central rib.

*Margin.*—Big, saw-formed crenation.

*Pubescence.*—Upper surface: Light. Lower surface: Light.

*Color.*—Young leaves: Upper surface: Dark red. Lower surface: Light lilac. Mature leaves: Green with a dull tint.

*Length*.*—9.2 cm.

*Width*.*—5.2 cm.

*Form*.*—Ovate.

*Texture*.*—Smooth.

*Thickness*.*—Moderate.

*Apex*.*—Acute.

*Base*.*—Mostly symmetrical.

*Margin*.*—Serrate.

*Pubescence*.*—Upper surface*: Slight to none. Lower surface*: Moderate.

*Color*.*—New, young leaves*: Upper surface*: 187A. Lower surface*: 187A. Mature leaves*: Upper surface*: 139B. Lower surface*: 139C.

*Petiole.*—Length: Short. Diameter: Average. Color: 143A. Shape*: Straight. Length*: 1.0 cm.

*Veins.*—Venation description: Central rib is slightly raised. Venation description*: Net-like. Color*: 60C.

Flower buds:

*Pedicel.*—Length: 1.5 cm. Diameter: 3.0 mm. Color: Dark lilac.

*Bud.*—Length: 1.5-2.0 cm. Width: 0.7 cm. Color: Dark; wine-like.

*Dormant bud*.*—Length*: 3.0 mm. Width*: 2.0 mm. Color*: 202C.

Flowers:

*Bloom timing.*—From May 9th to May 25th; average is May 13th to May 15th.

*Blooming period.*—10 to 12 days.

*Pollination.*—Cross.

*Fragrance.*—Faint.

*Petals.*—Number: 5. Length: 1.2-1.5 cm. Width: 0.7-1.0 cm. Color (generally 143A): When opening: Upper surface: Dark; wine-like. Lower surface: Dark pink. Fully opened: Upper surface: Bright pink. Lower surface: Dark pink.

*Pollen color: Dark cherry colored.*

Fruit:

*Date of picking.*—Aug. 15, 2008.

*Size.*—Axial diameter: 2.5-3.0 cm. Transverse diameter: 2.0-3.5 cm. Form: Rounded.

*Cavity.*—Depth: 4.0-5.0 mm. Breadth: 10.0 mm.

*Basin.*—Depth: Little. Width: Narrow.

*Skin.*—Thickness: Thin. Tendency to crack: Not recorded. Color: Dark red.

*Flesh.*—Aroma: Absent. Color: Dark red. Eating quality: Mediocre, not edible, astringent tasting.

*Seeds.*—Number perfect: 5. Number in one cell: 1 to 2. Length: 5.0 mm. Breadth: 4.0-5.0 mm. Form: Round and elongated. Color: Reddish-brown.

*Stem length.*—25.0-30.0 mm.

*Use.*—For processing.

*Shipping quality.*—Weak.

*Keeping quality.*—Very poor.

Tree winter hardiness: High.

Bud winter hardiness: High.

Drought tolerance: Average.

MULTIPLICATION ABILITY

Layering: Vertical; horizontal.

Hardwood cuttings: Good multiplication by hardwood and root cuttings.

Softwood cuttings: Good in the greenhouse.

PATHOGEN RESISTANCE

Fungal disease: High.

Insects: High.

PERFORMANCE AS ROOTSTOCK UPON GRAFTING

Root sprouts (suckering): Very good, fibrous roots.

Anchorage: Sufficient.

Compatibility: No recorded incompatibilities to date.

Vigor: The rootstock induces dwarfing of the scion variety grafted onto it.

I claim:

1. A new and distinct variety of *Malus domestica* rootstock, as illustrated and described herein.

* * * * *